US 6,645,523 B2

(12) United States Patent
Lemmens et al.

(10) Patent No.: US 6,645,523 B2
(45) Date of Patent: Nov. 11, 2003

(54) PAROXETINE COMPOSITIONS AND PROCESSES FOR MAKING THE SAME

(75) Inventors: Jacobus M. Lemmens, Mook (NL); Theodorus H. A. Peters, Arnhem (NL); Frantisek Picha, Brno (CZ); Johannes J. Platteeuw, 's-Hertogenbosch (NL); Frans van Dalen, Nijmegen (NL)

(73) Assignee: Synthon BCT Technologies, LLC, Chapel Hill, NC (US)

( * ) Notice: Subject to any disclaimer, the term of this patent is extended or adjusted under 35 U.S.C. 154(b) by 0 days.

(21) Appl. No.: 09/939,561

(22) Filed: Aug. 28, 2001

(65) Prior Publication Data

US 2002/0065301 A1 May 30, 2002

Related U.S. Application Data

(60) Provisional application No. 60/228,110, filed on Aug. 28, 2000, and provisional application No. 60/234,936, filed on Sep. 26, 2000.

(51) Int. Cl.⁷ .............................. A61K 9/48; A61K 9/14; A61K 9/16; A61K 9/20; A61K 9/46
(52) U.S. Cl. ...................... 424/451; 424/464; 424/465; 424/466; 424/489; 424/493; 424/494; 424/497
(58) Field of Search .................................. 424/451, 464, 424/465, 466, 489, 493, 494, 497

(56) References Cited

U.S. PATENT DOCUMENTS 5,102,666 A * 4/1992 Acharya
6,113,944 A * 9/2000 Pathak et al.

FOREIGN PATENT DOCUMENTS

| DE | 299 21 300 U1 | * 2/2000 |
| WO | WO 99/65491 | * 12/1999 |
| WO | WO 00/78291 | * 12/2000 |

* cited by examiner

Primary Examiner—Thurman K. Page
Assistant Examiner—Simon J. Oh
(74) Attorney, Agent, or Firm—Fleshner & Kim, LLP

(57) ABSTRACT

Paroxetine salt compositions having improved stability are formed by controlling the pH to 6.5 or less. The compositions can be made with the aide of water without significant coloration problems. The paroxetine salts include paroxetine hydrochloride salts but preferably use paroxetine sulfonate salts such as paroxetine methane sulfonate.

36 Claims, No Drawings

PAROXETINE COMPOSITIONS AND PROCESSES FOR MAKING THE SAME

CROSS-REFERENCE TO RELATED APPLICATIONS

This application claims the benefit of priority under 35 U.S.C. §119(e) from prior U.S. provisional application Ser. No. 60/228,110 filed Aug. 28, 2000 and from prior U.S. provisional application Ser. No. 60/234,936 filed Sep. 26, 2000: the entire contents of each of the aforementioned provisional applications being incorporated herein by reference.

BACKGROUND OF THE INVENTION

1. Field of the Invention

The present invention relates to a paroxetine compositions, especially pharmaceutical formulations and dosage forms, and to processes of manufacturing the same.

2. Description of the Related Arts

U.S. Pat. No. 4,007,196 describes certain compounds that possess anti-depressant activity. One specific compound mentioned in this patent is known as paroxetine and is represented by the following formula:

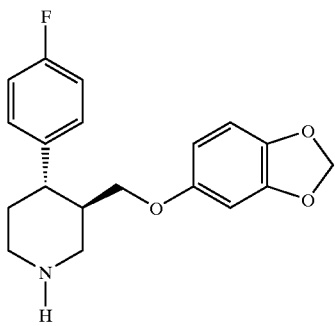

Paroxetine has been approved for treating, inter alia, depression in humans and is being marketed around the world under such brand names as Paxil® (SmithKline Beecham) and Seroxat. Dosage forms thus far include immediate release tablets, extended release tablets, capsules and suspensions. The active substance in all commercial forms thus far has been paroxetine hydrochloride and specifically with regard to tablets and other solid forms the active has been paroxetine hydrochloride hemihydrate as disclosed in U.S. Pat. No. 4,721,723 and EP 223403.

WO 95/16448 reports that all commercial paroxetine hydrochloride hemihydrate tablets were, at least up until that time, made using a wet granulation process. Further, the commercial tablets exhibited a color change; i.e., these tablets often developed a pink hue that is highly undesirable. This was apparently masked in the commercial product by a colored outer coat layer. The point of the PCT publication is that the pink hue formation can be avoided by carrying out tableting in the absence of water, i.e. by conventional dry granulation and direct compression. The PCT publication does not mention what the coloring compound(s) are or their route of formation. But, subsequent documents reveal that the coloration problem involves the formation of a coloring impurity identified below as the compound of formula A.

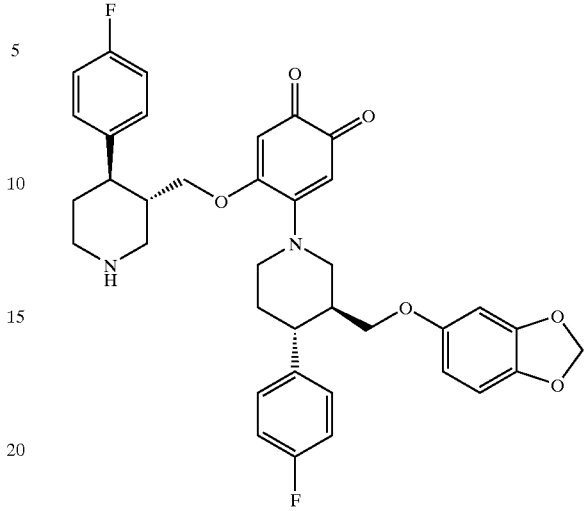

Since the publication of WO95/16448, it appears that the brand name paroxetine hydrochloride hemihydrate product in Europe, at least, was changed to a dosage form made by a dry granulation technique in accordance with the teachings in the PCT publication.

It would be advantageous to find a paroxetine composition that does not suffer from coloration or that is less prone to coloration regardless of how the composition is made. Further, it would be desirable to make a paroxetine composition with the aid of water, such as by wet granulation, that nonetheless was not prone to the above-mentioned coloration problems.

In particular, the application of an aqueous granulation process for industrial scale production is desirable in that such a process provides uniform distribution of the active substance within the bulk granulate composition so that the dose uniformity of tablets or capsules is more easily assured. This is especially true in the case of unit dosage forms containing a low dose of a potent active agent. Here, paroxetine is normally used in 20 to 40 mg per tablet and thus its uniformity in large scale production could be of concern. Water is a very suitable solvent for the granulation process because it is non-toxic and non-flammable. Thus, it would be desirable to find a way to use an aqueous granulation process for the industrial scale production of paroxetine final forms that would also avoid or limit the occurrence of the color forming impurities.

U.S. Pat. No. 5,874,447 describes paroxetine sulfonate salts, including paroxetine methane sulfonate also known as paroxetine mesylate. These sulfonate salts have advantageous properties in comparison to the known salts, including the hydrochloride salts. For example, the sulfonate salts have high water solubility and good thermal stability, making them useful in forming a commercial paroxetine dosage form. The U.S. Pat. No. 5,874,447 patent discloses that tablets can be made by any known method including a dry technique (direct compression, dry granulation) or a wet technique (wet granulation). However, no discussion appears in the U.S. Pat. No. 5,874,447 patent regarding the paroxetine hydrochloride coloring problem.

SUMMARY OF THE INVENTION

Now, it has surprisingly been discovered that solid paroxetine compositions including granulates and dosage forms made therefrom, can be made more stable against coloration, even if made with the aid of water such as by an aqueous granulation process, by controlling the pH of the composition to 6.5 or less. Further, it appears that paroxetine sulfonate salts are less prone to coloration problems than paroxetine hydrochloride salts, even if made with the assistance of water. Studies by the present inventors reveal that the impurity A is a dimer formed from the paroxetine free base in an aqueous alkaline environment. Oxygen is also apparently needed to allow the dimer reaction to proceed. Given the discovery that coloring impurity A is formed in the presence of water, it is understandable in hindsight how carrying out a dry process as suggested in WO95/16448 would help to minimize and/or avoid coloration; i.e. the required aqueous medium for forming the dimeric impurity is missing thereby inhibiting its formation. Having elucidated the source of the coloring problem, the present invention provides a novel solution thereto by keeping the pH of the composition to 6.5 or less. Alternatively, the present invention unexpectedly solves the coloring problem by switching the paroxetine salt from hydrochloride to sulfonate and thereby allowing the use of water in the preparation of paroxetine granules without incurring any substantial coloration.

Thus, in a first aspect of the invention, there is provided a solid paroxetine composition comprising a paroxetine salt and an excipient wherein said composition has a pH of 6.5 or less, as is hereinafter defined. The paroxetine salt is preferably a paroxetine sulfonate salt such as paroxetine methane sulfonate or a paroxetine hydrochloride salt. The excipients generally include a binder or diluent such as calcium phosphate or microcrystalline cellulose as well as a disintegrant and lubricant. The composition can be an intermediate form or a final dosage form such as a tablet or capsule. In one embodiment, a tablet is made that does not need a taste masking coating to avoid the usual bitter taste associated with paroxetine compositions.

A second aspect of the present invention relates to paroxetine solid dosage forms comprising a paroxetine sulfonate salt as a pharmaceutically active agent and having been made with the aid of water. The solid dosage form can be a tablet, pellet or capsule form, etc., and contains a pharmaceutically effective amount of paroxetine sulfonate, e.g. for treating depression, obsessive-compulsive disorder, or panic attack, etc. Preferably the excipients are selected so that the composition has a pH of 6.5 or less. Further, the composition is normally dried to a sufficient extent that the total content of added water remaining is 2.0 wt % or less, preferably 1.3 wt % or less, and more preferably 1.0 wt % or less. Generally, the composition does not contain any decolorization agent as an excipient. Even though an aqueous process is used, the dosage form of the present invention exhibits no, or substantially no, formation of a pink or other colored hue.

A third aspect of the invention provides for a granulate formed by mixing water, paroxetine sulfonate salt, and at least one excipient and drying the resulting mixture. Typically the water and paroxetine sulfonate salt are provided together as an aqueous solution and added to the powdered or dry excipient(s), although this is not required. In some embodiments, the excipient(s) may be pre-blended and granulated such as by a dry granulation technique before being contacted with a concentrated aqueous paroxetine sulfonate salt solution. The mixture is dried to form a granulate to which additional excipients may be added, if desired. The granulate can be formed into other conventional dosage forms such as tablets, capsules, sachets, pellets, etc.

The composition is preferably selected as described above for the dosage forms, namely with a pH of 6.5 or less and with an added water content of 2.0 wt % or less.

A fourth aspect of the invention provides a process for making pharmaceutical compositions which comprises mixing paroxetine sulfonate and at least one excipient with the aid of water. In one convenient embodiment, an aqueous solution containing at least 10 wt % of a paroxetine sulfonate salt is added to at least one solid excipient and dried to form a granulate. Preferably, the aqueous solution is a highly concentrated aqueous solution of paroxetine sulfonate salt having a concentration of not less than 30 wt %. This process can be used advantageously to form the granulates described above which can be subsequently processed into the above-described dosage forms. Alternatively, water can be added to a powder bed of paroxetine sulfonate and one or more excipients and the mixture dried to form granules.

A preferred paroxetine sulfonate salt for use in all aspects of the present invention is paroxetine methanesulfonate, also called paroxetine mesylate. Paroxetine mesylate is compatible with many common pharmaceutical excipients useful in aqueous granulation procedures, which makes the process reliable on an industrial scale.

DETAILED DESCRIPTION OF THE INVENTION

The present invention relates to solid paroxetine compositions that resist the formation of a color hue and to processes for making the same with the aid of water. As used herein, the expression "made with the aid of water" means that water is added during some aspect of the formation process of the composition but is substantially or completely removed in the final composition. The water can be added to excipients, to the paroxetine salt especially paroxetine sulfonate salts, or to both. The solid compositions of the invention include solid dosage forms such as tablets, capsules, sachets, etc., and intermediate forms such as granules or pellets.

Paroxetine salts used in the present invention are pharmaceutically acceptable salts, i.e., acid addition salts. Preferred salts include paroxetine hydrochloride salts and paroxetine sulfonate salts. The paroxetine hydrochloride salt can be of any form including the paroxetine hydrochloride hemihydrate form and paroxetine hydrochloride anhydrate forms. The paroxetine sulfonate salts used in the present invention can be any salt of paroxetine where the an anion contains a sulfonate group; i.e. the moiety —S(O$_2$)OH. Preferred sulfonate salts include those having the following structural formula:

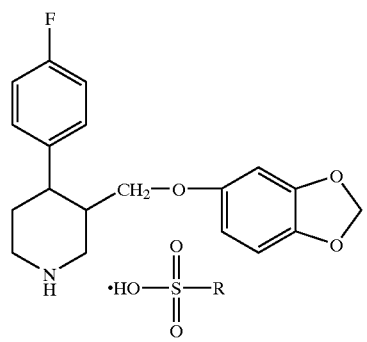

wherein R represents a C$_1$–C$_{10}$ substituted or unsubstituted alkyl group or a substituted or unsubstituted aromatic group wherein the substituents are selected from the group consisting of $C_1$–$C_{10}$ alkyl, halogen, nitro, hydroxy, alkoxy, and combinations thereof. Preferred paroxetine sulfonate salts include those having a solubility in water of at least 100 mg/1 ml of water. Particularly preferred sulfonate salts include methanesulfonate, ethanesulfonate, benzenesulfonate and p-toluenesulfonate salt forms.

An "excipient" as used herein means any pharmaceutically acceptable inactive component of the composition. As is well known in the art, excipients include diluents, binders, lubricants, disintegrants, colorants, preservatives, pH-adjusters etc. The excipients are selected based on the desired physical aspects of the final form: e.g., obtaining a tablet with desired hardness and friability, being rapidly dispersible and easily swallowed, etc. The desired release rate of the active substance from the composition after its ingestion also plays a role in the choice of excipients.

Suitable excipients for use in this invention include:

a diluent such as calcium hydrogen phosphate, lactose, mannitol etc.

a binder such as microcrystalline cellulose or a modified cellulose, povidone etc.

a disintegrant such as sodium starch glycollate, crosspovidone a lubricant such as magnesium stearate, sodium stearyl fumarate a colorant, taste masking agent etc.

It is particularly advantageous that the composition of the invention is not specifically required to use anhydrous excipients or hydrophobic excipients, although such excipients may be used. Similarly, the present invention does not have to strictly control the water content in the excipients prior to their use or incorporation. In a preferred embodiment, no decolorization agent is required to be present in the composition of the invention, although such may be present if desired. "Decolorization agent" as used herein means an agent which is being added to a composition with the aim to protect the active substance against reactions that form colored products, such as an antioxidant (e.g. ascorbic acid etc.), free radical scavenger (e.g. tocopherol etc.) etc.

It has now been discovered that the undesired impurity A is preferentially formed in an aqueous alkaline environment from the paroxetine free base. Accordingly, it can be advantageous to employ multiple strategies to reduce or prevent coloration. These strategies include limiting the amount of added water remaining in the composition, controlling the pH of the composition to be sufficiently acidic, limiting the presence of oxygen during formation and/or storage, and reducing the level of paroxetine free base impurity in the active. Indeed, using one or more of these strategies can control the coloring problem encountered with other paroxetine salt forms including paroxetine hydrochloride salt forms, whether made from a dry or wet process. For example controlling the pH to 6.5 or less, controlling (reducing) the level of free base impurity, and/or quickly removing 98% or more of the water used in granulating should allow for the formation of a color stable paroxetine hydrochloride pharmaceutical composition. Additionally, for reasons that are not entirely clear, paroxetine sulfonate salts can provide superior color stability in comparison to paroxetine hydrochloride salts.

The compositions of the present invention, including granulates and final dosage forms, preferably have a pH of 6.5 or less, more preferably a pH of 6.0 or less, including about 5.5 or less. Typically, the pH of the dosage form or a granulate is within the range of 4.5 to 6.5, more typically from 5.0 to 6.0. The pH is determined by forming a slurry of the solid composition with water and measuring the pH of the slurry, as is understood by workers skilled in the art regarding the pH of a solid composition. The concentration of the composition in the slurry is 20 wt %. The pH is measured by any standard technique. The pH can be adjusted by the proper selection of excipients.

In this respect, a proper grade of calcium phosphate (anhydrous or hydrated) having a pH around 5.5 is preferred to be used as a suitable filler. Commercially available/pharmaceutically acceptable calcium phosphates are generally alkaline; i.e. pH greater than 7 when measured as described above in a 20% slurry. For instance, DI-TAB, a commercially available dibasic calcium phosphate dihydrate, is reported as having a pH of about 7.4. Nonetheless some forms and grades of calcium phosphate are acidic or neutral pH. This lower pH can be due to the species of calcium phosphate as well as the treatment during processing of the material, such as in removing impurities/washing. For example, dibasic calcium phosphate anhydrate is generally considered to have a pH of about 7.3 whereas A-Tab™ (Rhodia), also a dibasic calcium phosphate anhydrate, has a pH of about 5.1. Further examples of commercially available non-alkaline calcium phosphates include DiCAFOS P (Budenheim) having a pH of about 7 and Fujicalin SG (Fuji) having a pH from 6.1–7.2. By using a non-alkaline calcium phosphate as an excipient, a pharmaceutical composition meeting the desired pH can be attained. Alternatively, a blend of calcium phosphates, even one using acidic and alkaline calcium phosphates, can be used to achieve the desired acidic pH of the composition. The pH can also be assisted by selection of any other excipients in the composition. For instance, another example of a useful acidic excipient is the disintegrant Explotab(™) of Penwest, which is a cross-linked, low substituted sodium starch glycollate.

Especially advantageous compositions of the invention comprise paroxetine sulfonate salt in the absence of a hydrosoluble or hydrophilic diluent such as lactose or microcrystalline cellulose. Unlike the suggestions in CH 690 024, wherein such a hydrosoluble/hydrophillic diluent is taught for use with paroxetine mesylate, it has been discovered that surprisingly the use of only a calcium phosphate diluent, such as calcium hydrogen phosphate anhydrate, exhibits an additional advantageous feature for industrial application; namely that it efficiently masks or prevents the bitter taste of paroxetine. Thus, after the paroxetine salt, especially paroxetine mesylate, and diluent composition is mixed with a disintergant and a lubricant and compressed into tablets, the tablets may be administered to a human patient without need of a taste-masking coating or a similar tool for taste masking. To the contrary, the presence of a hydrosoluble or hydrophilic diluent rather pronounces the bitter taste of paroxetine so that such tablet is unpleasant to be swallowed unless film-coated. Pharmaceutical compositions comprising paroxetine methane sulfonate and calcium hydrogen phosphate, optionally containing conventional lubricants and/or disintegrants, form a particular aspect of our invention. Of course, these particular compositions can be made by a dry process (dry mixing followed by direct compression) as well as by any of the wet processes known or described herein, and still provide the unexpected taste masking result.

In general, the compositions of the present invention preferably have a remaining added water content of 2.0 wt % or less, preferably 1.3 wt % or less, more preferably 1.2 wt % or less, still more preferably 1.0 wt % or less, and most preferably 0.8 wt % or less. The "remaining added water" content refers to the remaining water that was added in the aid of mixing and does not include water that was present in the excipients such as bound water in microcrystalline cellulose. If the composition was made by a dry process, then the remaining added water content is 0.0%. Generally, each formulation has a threshold amount of remaining added water content below which the dimeric impurity A is formed either very little or not at all. Above this threshold amount, the impurity A is formed abundantly. The occurrence of the impurity is thus not usually a linear function of water content. By controlling the added water content in the final granulate, a color stable product can be attained, even if made by a conventional wet granulation process. The same is true for the final product solid dosage form.

Granules made according to the present invention can be used directly but usually are processed into any of a variety of dosage forms as mentioned above. Typically, the granules, optionally with additional excipients, are compressed into tablets. The paroxetine tablets may be coated by a suitable film-coating, e.g., similar to the coating used in the commercially available tablets of paroxetine hydrochloride hemihydrate. Suitable techniques of coating include aqueous coating, non-aqueous coating or a melt coating process. Coating mixtures are commercially available. Coating for extended or delayed release of the active substance is also applicable to the composition of our invention. Coating mixtures may contain suitable colorants.

The paroxetine-containing granulate may also be used for preparation of capsulized unit dosage forms. The dry granulate may be optionally screened and/or pelletized by methods known per se to obtain particulate material of uniform size and shape. The granules or pellets are then filed into suitable capsules made from e.g. gelatine, hydroxypropylmethyl cellulose or starch. Capsules having low moisture content are preferred. Coating of the produced granulate is normally not necessary.

Paroxetine-containing granulate may also be filled into sachets containing the required unit dose of paroxetine. Such sachets are administered by dispersing or dissolving the content thereof in a suitable liquid, e.g. in water, and drinking. The compositions may contain suitable taste-masking excipients, flavors or sweeteners.

Another suitable final form comprising granulates according to the present invention are effervescent tablets, granulates or powders. They are formed by mixing the granulate with a suitable effervescent system by methods known per se.

The compositions of the present invention can be made by any conventional process including dry process such as dry blending, dry granulation, and direct compression as well as by wet processes such as wet granulation. In some embodiments, especially for paroxetine sulfonate salts, it is preferable to use water in the aide of mixing. For example, a granulate is formed by combining a paroxetine sulfonate salt and at least one excipient and mixing them in the presence of added water, followed by drying to remove substantially all of the added water. The resulting population of granules, or the "granulate," is dried to have a an average content of remaining "added water" of 2.0 wt % or less, preferably 1.3 wt % or less, more preferably 1.0 wt % or less and even 0.8 wt % or less, based on the total weight of the granulate.

Typically the water is added in one of two ways, although the invention is not limited thereto. In a first method, water is added to paroxetine sulfonate and an excipient. The amount of water added is normally between 5 and 25 wt %, more typically between 10 and 20 wt %, based on the total weight of the resulting wet mixture. More water can be added, i.e., 30 wt %, 40 wt % or even 50 wt %, but some difficulties may be encountered concerning possible modifications of the excipient (for instance microcrystalline cellulose may change crystal form) and additional energy will be needed to remove the higher amounts of added water. The paroxetine sulfonate salt and the excipient are normally in powder form and pre-mixed or blended to form a powder bed prior to the addition of water. Alternatively, the excipient can be in granulate form and admixed with the paroxetine sulfonate powder. The excipient is generally one or more diluents such as calcium phosphate, microcrystalline cellulose, or both.

The wet mixture is stirred, usually under vigorous conditions, to form a homogeneous mixture. The added water is removed from the wetted mixture normally as rapidly as possible. The added water can be removed by heating as well as by passing a nitrogen gas stream over (or through) the mixture, or a combination thereof. The use of a nitrogen gas stream is also advantageous in that the presence of oxygen is reduced or avoided. The drying of the added water can occur after, during or simultaneously with the mixing/stirring step. To reduce the chance of color formation, the average residence time of the added water in contact with the paroxetine sulfonate and excipient(s) during the mixing and drying steps is generally less than 3 hours, more typically less than 2 hours, more typically less than 1.5 hours, frequently less than or equal to 1 hour and is normally in the range of 30 to 90 minutes, more preferably 30 to 60 minutes, depending upon the apparatus volumes, etc. Upon completion of the stirring and drying steps, a paroxetine sulfonate-containing granulate is obtained having a low added water content as described above.

For preparation of a final mixture for compressing into a tablet core (pre-compression mixture), the above paroxetine sulfonate-containing granulate is optionally mixed with additional diluent(s), a disintegrant and/or a lubricant such as magnesium stearate, in a suitable mixer, e.g. in a free-fall mixer. The pre-compression mixture is finally compressed into tablets by a suitable tableting press under ordinary conditions. The other excipients for mixing with the granulate should also be chosen, in terms of kind and grade, such that the final pre-compressing mixture exhibits a pH value of 6.5 or less as described above.

A second method for forming the granulate involves combining the added water with the paroxetine sulfonate to form an aqueous solution of paroxetine sulfonate. This aqueous solution is then added to at least one excipient. As in the first method, the excipient can be in powder or granulate form. The aqueous solution is generally a concentrated solution having at least 10 wt % paroxetine sulfonate, preferably at least 30 wt %, and more preferably at least 40 wt % paroxetine sulfonate. By using a concentrated solution, less water is needed, thereby saving energy in the drying step and allowing for faster drying times. These highly concentrated solutions are possible because of the advantageous water solubility of paroxetine sulfonate in comparison to other paroxetine salts such as paroxetine hydrochloride. The stirring and drying steps as well as the work up of the granulate into a pre-compression composition are carried out as described above.

A preferred formulation made by this process comprises adding the concentrated paroxetine sulfonate aqueous solution to either calcium hydrogen phosphate or microcrystalline cellulose followed by stirring and drying to form a paroxetine-containing granulate. To the formed granulate is then mixed the other one of the calcium hydrogen phosphate or microcrystalline cellulose which was not used to form the granulate along with sodium starch glycolate (a disintegrant) and magnesium stearate. The resulting mixed composition is ready for compression into tablets. An example of this composition contains 7.24 wt % paroxetine sulfonate (as the equivalent free base), 57.76 wt % of $CaHPO_4$, 30.0 wt % microcrystalline cellulose (Avicel PH 101), 4.0 wt % sodium starch glycolate, and 1 wt % magnesium stearate.

In the aqueous granulation procedure for preparation of tablets or capsules of paroxetine mesylate, microcrystalline cellulose and various forms and grades of calcium phosphate, typically calcium hydrogen phosphate, are the preferred solid diluents. However, the composition of this invention and the process for its preparation is not limited thereto. Alternate diluents include mono- and di saccharide sugars such as lactose, mannitol, lactitol, xylitol or combinations thereof.

Alternatively, a dry process can also be carried out wherein the paroxetine salt is dry blended with an excipient, typically a calcium phosphate or microcrystalline cellulose, or both and optionally with a disintegrant. After blending, the mixture is compressed into a tablet.

For both wet and dry processes, it is sometimes advantageous to provide multiple mixing steps to facilitate high quality, homogenous mixing. For example, a portion of the binder(s) and/or disintegrant(s) are mixed with the paroxetine salt, optionally with the aide of water as described above. To this mixture the remainder of the binder(s) and/or disintegrant(s) are mixed. To this resulting mixture the remaining excipients such as a lubricant(s) are mixed. Such partial mixing can use more steps or fewer steps and can split intermediate mixtures into portions to facilitate apparatus volumes. Additionally, excipients can be pre-treated by techniques known in the art as desired, including wet granulation and dry granulation treatments. The binders or fillers such as calcium phosphate anhydrate can be pre-treated with water and dried (<0.5% water) before being combined with the paroxetine salt or solution.

The composition of the present invention can be used to treat or prevent the following disorders: depression, obsessive compulsive disorder, alcoholism, anxiety, panic disorder, chronic pain, obesity, senile dementia, migraine, bulimia, anorexia, social phobia, pre-menstrual syndrome, adolescent depression, trichotillomania, dysthymia, substance abuse etc. Most suitably, the composition of the invention is applied for treatment of depression, obsessive compulsive disorder and panic disorder.

The treatment or prevention of any one or more of the above disorders is performed by administering orally the composition comprising an effective and/or prophylactic amount of the paroxetine sulfonate to a patient in need thereof. The patient can be a mammal including a human, a dog, a horse, or a monkey.

The composition of this invention is advantageously presented as a unit dose composition, preferably in a form of a tablet or a capsule, comprising paroxetine sulfonate equivalent to from 1 to 200 mg of paroxetine free base, more usually from 5 to 100 mg, for example from 10 to 50 mg. Typical tablet doses are 10, 20, 30, and 40 mg. Such a composition is normally taken by a human patient from 1 to 6 times daily, but more usually once or twice daily, with the total amount of paroxetine sulfonate administered being generally between 5 to 400 mg of paroxetine. A suitable daily dose is from 0.05 to 6 mg/kg, more preferably 0.14 to 0.86 mg/kg.

EXAMPLES

Example 1

Granulate of Paroxetine Mesylate for Tablet Production

1. Prepare a pre-blend of 3177.5 g of calcium hydrogen phosphate anhydrate (A-TAB pH 5.1) and 29.75 g of sodium starch glycollate by mixing for 5 minutes in a high-shear granulator.
2. Prepare a solution of 258.3 g of paroxetine mesylate in 350 ml of water.
3. Add the solution to the pre-blend granulate from the step 1 at ambient temperature.
4. Dry the wet granulate at 40° C. under diminished pressure and nitrogen flow to less than 1% water content.
5. Mix the resulted granulate with 29.75 g of sodium starch glycollate for 15 minutes in a free-fall mixer; add 70.0 g of magnesium stearate to the mixture and mix for 5 minutes.

Tablet cores containing 40 mg of paroxetine are prepared from the resulting granulate (pH=5.53) on a suitable tableting machine (tablet weight 713 mg, punch diameter 10 mm, hardness 80 N). Despite the use of water to aid in the mixing, these tablets did not turn pink upon storage under accelerated conditions (40° C./75% RH) packaged in PVC/PE/PVDC-aluminium blisters or in HDPE containers.

Example 2

Granulate of Paroxetine Mesylate for Tablets

The process as in Example 1 was maintained with the modification that the steps 3 and 4 are performed simultaneously, at 40° C. The time necessary for adding the paroxetine mesylate aqueous solution is approx. 15 minutes; for drying approx. 45 minutes. The composition has a pH of 5.37.

Example 3

Tablets of paroxetine mesylate are made having the following composition:

| Paroxetine mesylate | 12.915 mg (10 mg equiv.) | 25.83 mg (20 mg equiv.) | 38.745 mg (30 mg equiv.) | 51.66 mg (40 mg equiv.) |
| --- | --- | --- | --- | --- |
| Calcium hydrogen phosphate anhydrate pH 5.1 | 158.88 mg | 317.75 mg | 476.64 mg | 635.50 mg |
| Sodium starch glycollate | 2.975 mg | 5.95 mg | 8.925 mg | 11.90 mg |
| Magnesium stearate | 3.50 mg | 7.00 mg | 10.50 mg | 14.00 mg |

The tablets are made as follows. Paroxetine mesylate is mixed with calcium hydrogen phosphate. 10% water is added and the mixture granulated and dried to an added water content of around 1%. The resulting granulate is mixed with the sodium starch glycollate, and magnesium stearate in a free fall mixer and compressed into tablets; each tablet having the above composition. The pH varies from 5.2 to 5.8 depending upon the batches of excipients used.

Example 4

Tablets of Paroxetine Mesylate

| | |
|---|---|
| Paroxetine mesylate | 51.66 mg |
| | (equivalent to 40 mg of |
| | paroxetine free base) |
| Calcium hydrogen phosphate | 411.83 mg |
| Microcrystalline cellulose | 213.92 mg |
| Sodium starch glycollate | 28.52 mg |
| Magnesium stearate | 7.13 mg |

Tablets having the above composition are made as follows. Paroxetine mesylate is mixed with calcium hydrogen phosphate. 10% water is added and the mixture granulated and dried to an added water content of around 1%. The resulting granulate is mixed with microcrystalline cellulose, sodium starch glycollate, and magnesium stearate in a free fall mixer and compressed into tablets; each tablet having the above composition. The pH is 5.45.

Example 5

The same tablets as Example 4 are made, but first a paroxetine mesylate aqueous solution having a paroxetine mesylate concentration of about 30 wt % is formed. This solution is added to microcrystalline cellulose and dried to form a granulate. The produced granulate is mixed with calcium hydrogen phosphate, sodium starch glycollate, and magnesium stearate in a free fall mixer and compressed into tablets. The pH is 5.26.

Example 6

Tablets of Paroxetine Mesylate
Composition per 1 g of tablet core:

| | |
|---|---|
| Paroxetine mesylate | 72 mg |
| Mannitol | 300 mg |
| Calcium hydrogen phosphate | 533 mg |
| Croscarmellose sodium | 20 mg |
| Povidone | 30 mg |
| Magnesium stearate | 15 mg |

1. Granulate 30% solution of paroxetine mesylate with a pre-blend mixture of mannitol, calcium hydrogen phosphate and croscarmellose sodium and dry to water content less than 1%.
2. Mix the dried and screened granulate with povidone and magnesium stearate. The granulate is suitable for compression into tablets containing 20 mg paroxetine.

Example 7

Tablets of Paroxetine Mesylate
Composition of 1 g of tablet core:

| | |
|---|---|
| Paroxetine mesylate | 72 mg |
| Microcrystalline cellulose | 290 mg |
| Calcium hydrogen phosphate | 580 mg |
| Sodium starch glycollate | 28 mg |
| Hydroxypropyl cellulose | 20 mg |
| Magnesium stearate | 10 mg |

1. Granulate 30% aqueous solution of paroxetine mesylate with a pre-blend mixture of microcrystalline cellulose, calcium hydrogen phosphate and sodium starch glycollate and dry.
2. Mix the dried and screened granulate with hydroxypropyl cellulose and magnesium stearate.

The granulate is suitable for compression into tablets containing 20 mg paroxetine and having a pH of 5.14.

In the following Examples 8–19, the compositions listed are processed substantially as in Example 1, e.g. a granulate is prepared by using a concentrated aqueous solution of paroxetine mesylate and the dry paroxetine mesylate-containing granulate with water content less than 1% is mixed with the remaining excipients to prepare a bulk material for processing into the listed final forms by conventional methods.

Example 8

| Composition of effervescent tablets (per 1 g) | |
|---|---|
| a) granulate | |
| Paroxetine mesylate | 26 mg |
| Mannitol | 166 mg |
| b) Effervescent system | |
| Sodium bicarbonate | 378 mg |
| Citric acid anhydrous | 400 mg |
| Saccharin sodium | 9 mg |
| Aspartame | 3 mg |
| Sodium chloride | 1.5 mg |
| Sodium lauryl sulfate | 0.05% |
| Flavour | 16 mg |

Example 9

| Composition of effervescent tablets (per 1 g) | |
|---|---|
| a) granulate | |
| Paroxetine mesylate | 26 mg |
| Isomaltose | 203 mg |
| b) Effervescent system | |
| Sodium bicarbonate | 336 mg |
| Citric acid | 400 mg |
| Sodium chloride | 1.5 mg |
| Neo-DHC | 5 mg |
| Sodium lauryl sulfate | 0.5 mg |
| Flavour | 18 mg |

Example 10

| Composition of dispersible tablets (per 1 g) | |
|---|---|
| a) granulate | |
| Paroxetine mesylate | 72 mg |
| Pregelatinized starch | 380 mg |
| Microcrystalline cellulose | 380 mg |
| Sodium starch glycollate | 100 mg |
| b) Other excipients | |
| Hydroxypropyl cellulose | 20 mg |
| Sodium saccharin | 8 mg |
| Sodium stearyl fumarate | 10 mg |
| Colloidal silicine dioxide | 10 mg |
| Flavour | 20 mg |

Example 11

| Composition of dispersible tablets (per 1 g) | |
|---|---|
| a) granulate | |
| Paroxetine mesylate | 72 mg |
| Mannitol | 500 mg |
| Microcrystalline cellulose | 260 mg |
| Crosspovidone | 100 mg |
| b) Other excipients | |
| Sodium saccharin | 8 mg |
| Sodium stearyl fumarate | 10 mg |
| Colloidal silicon dioxide | 10 mg |
| Flavour | 20 mg |

Example 12

| Composition of sublingual tablets (per 1 g) | |
|---|---|
| a) granulate | |
| Paroxetine mesylate | 72 mg |
| Sucrose | 650 mg |
| Sorbitol | 258 mg |
| b) Other excipients | |
| Sodium stearyl fumarate | 20 mg |

Example 13

| Composition of sublingual tablets (per 1 g) | |
|---|---|
| a) granulate | |
| Paroxetine mesylate | 72 mg |
| Mannitol | 318 mg |
| Microcrystalline cellulose | 600 mg |
| b) Other excipients | |
| Magnesium stearate | 10 mg |

Example 14

| Composition of controlled release tablets with hydrophilic matrix (per 1 g) | |
|---|---|
| a) granulate | |
| Paroxetine mesylate | 72 mg |
| Hydroxypropylmethyl cellulose | 700 mg |
| Hydroxypropyl cellulose | 168 mg |
| b) other ingredients | |
| Povidone | 40 mg |
| Sodium stearyl fumarate | 20 mg |

Example 15

| Composition of controlled release tablets with hydrophobic matrix (per 1 g) | |
|---|---|
| a) granulate | |
| Paroxetine mesylate | 72 mg |
| Microcrystalline cellulose | 520 mg |
| b) other ingredients | |
| Glyceryl behenate | 200 mg |
| Glyceryl palmitostearate | 200 mg |
| Sodium stearyl fumarate | 8 mg |

Example 16

| Composition for immediate-release hard-shell capsules (per 1 g) | |
|---|---|
| a) granulate | |
| Paroxetine mesylate | 72 mg |
| Maltodextrin | 820 mg |
| Pregelatinized starch | 80 mg |
| b) other ingredients | |
| crosspovidone | 20 mg |
| colloidal silicone dioxide | 8 mg |

The produced granulate should be sieved and filled per 333 mg into Size 2 capsule.

Example 17

| Composition for enteric-release hard-shell capsules (per 1 g) | |
|---|---|
| a) granulate | |
| Paroxetine mesylate | 72 mg |
| Sucrose-starch non-pareill seeds | 790 mg |
| Eudragit L 30 D 55 | 123.5 mg |
| b) other ingredients | |
| talc | 7 mg |
| polyethylene glycol 6000 | 7 mg |
| silicone dioxide | 0.5 mg |

The produced granulate should be sieved and filled per 333 mg into Size 2 capsule.

Example 18

| Composition for controlled release hard-shell capsules (per 1 g) | |
|---|---|
| a) granulate | |
| Paroxetine mesylate | 72 mg |
| microcrystalline cellulose | 850 mg |
| Ethylcellulose | 60 mg |
| Hydroxypropylcellulose | 18 mg |
| b) other ingredients | |
| none | |

The produced granulate should be sieved and filled per 350 mg into Size 2 capsule.

Example 19

| Composition for oral sachets (per 1 g) | |
|---|---|
| a) granulate | |
| Paroxetine mesylate | 5 mg |
| Sucrose | 565 mg |
| Mannitol | 377 mg |
| Povidone | 28 mg |
| b) other ingredients | |
| saccharin sodium | 10 mg |
| Flavour | 15 mg |

The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

We claim:

1. A solid unit dose paroxetine composition comprising a pharmaceutically effective amount of a paroxetine hydrochloiride, an acidic calcium phosphate, and a disintegrant wherein said composition has a pH within the range of 4.5 to 6.0.

2. The composition according to claim 1, wherein said pH is within the range of about 5.0 to 5.8.

3. The composition according to claim 1, wherein said composition is a tablet.

4. The composition according to claim 3, which further comprises a lubricant, a colorant, or both.

5. The composition according to claim 4, which does not contain a hydrosoluble or hydrophilic diluent.

6. The composition according to claim 5, which does not contain a taste masking coating.

7. The composition according to claim 1, wherein said calcium phosphate constitutes at least 55% of said composition.

8. A granulate formed by mixing water, paroxetine sulfonate, and at least one excipient and drying the resulting mixture, wherein said mixing was accomplished by adding together an aqueous solution having at least about a 10 wt % concentration of paroxetine sulfonate with said at least one excipient.

9. The granulate according to claim 8, wherein said aqueous solution has a paroxetine sulfonate salt concentration of at least about 30 wt %.

10. The granulate according to claim 8, wherein said mixing and said drying are carried out simultaneously.

11. The granulate according to claim 8, wherein said aqueous solution of paroxetine sulfonate was added to a powdered or granulated blend of said at least one excipient.

12. The granulate according to claim 8, wherein said granulate has an average remaining added water content of about 2.0 wt % or less.

13. The granulate according to claim 12, wherein said granulate has an average remaining added water content of about 1.0 wt % or less.

14. The granulate according to claim 13, wherein said granulate has an average remaining added water content of about 0.8 wt % or less.

15. The granulate according to claim 8, wherein said granulate composition exhibits a pH value of 6.5 or less.

16. The granulate according to claim 15, wherein said granulate has a pH of about 6.0 or less.

17. The granulate according to claim 15, wherein said granulate has a pH within the range of 4.5 to 6.5.

18. The granulate according to claim 8, wherein said paroxetine sulfonate salt is paroxetine methane sulfonate.

19. A process, which comprises:

mixing an aqueous solution containing at least 10 wt % of a paroxetine sulfonate with at least one solid excipient; and drying to form a granulate.

20. The process according to claim 19, wherein said drying step produces a granulate having a remaining added water content of about 2.0 wt % or less.

21. The process according to claim 20, wherein said drying step produces a granulate having a remaining added water content of about 1.3 wt % or less.

22. The process according to claim 21, wherein said drying step produces a granulate having a remaining added water content of about 1.0 wt % or less.

23. The process according to claim 22, wherein said drying step produces a granulate having a remaining added water content of about 0.8 wt % or less.

24. The process according to claim 19, wherein said aqueous solution concentration of said paroxetine sulfonate is at least 30 wt %.

25. The process according to claim 24, wherein said aqueous solution concentration of said paroxetine sulfonate is at least 40 wt %.

26. The process according to claim 19, wherein said mixing and drying steps are performed concurrently.

27. The process according to claim 19, wherein said solid excipient is a granulate.

28. The process according to claim 19, which further comprises optionally mixing additional excipients with said granulate and pressing said granulate composition into a tablet.

29. The process according to claim 19, which further comprises film coating said tablet.

30. The process according to claim 21, which further comprises filling said granulate into a capsule or sachet.

31. The process according to claim 19, which further comprises processing said granulate into effervescent tablets, sublingual tablets, controlled release tablets or delayed release tablets.

32. The process according to claim 28 wherein the excipients comprise at least one ingredient selected from the group consisting of binders, disintegrants, and fillers.

33. The process according to claim 32, wherein said granulate exhibits a pH value of 6.5 or less.

34. The process according to claim 33, wherein said granulate has a pH of about 6.0 or less.

35. The process according to claim 33, wherein said granulate has a pH of about 5.5 or less.

36. The process according to claim 19, wherein said paroxetine sulfonate is paroxetine methane sulfonate.

* * * * *